United States Patent [19]
Posakony et al.

[11] Patent Number: 5,804,725
[45] Date of Patent: Sep. 8, 1998

[54] MEASUREMENT OF THE CURE STATE OF A CURABLE MATERIAL USING AN ULTRASONIC WIRE WAVEGUIDE

[75] Inventors: Gerald J. Posakony, Richland, Wash.; Yan Li, San Diego, Calif.

[73] Assignee: XXSYS Technologies, Inc., San Diego, Calif.

[21] Appl. No.: 632,016

[22] Filed: Apr. 15, 1996

[51] Int. Cl.$^6$ ............................ G01N 29/24; G01N 29/16
[52] U.S. Cl. ................................. 73/590; 73/597
[58] Field of Search .................................. 264/40.1, 40.6, 264/236, 257, 326, 494, 510; 364/475.03; 73/597, 599, 590, 602; 156/275.5

[56] References Cited

U.S. PATENT DOCUMENTS

| | | | |
|---|---|---|---|
| 4,559,810 | 12/1985 | Hinrichs et al. | 73/54 |
| 4,590,803 | 5/1986 | Harrold | 73/590 |
| 4,904,080 | 2/1990 | Afromowitz | 356/133 |
| 5,009,104 | 4/1991 | Johnson | 73/597 |

OTHER PUBLICATIONS

Ronald T. Harrold et al., "Strain Measurements Inside Composite Materials Using Embedded Acoustic Waveguides," Preprint of Publication presented at Conference on Nondestructive Evaluation Applied to Process Control of Composite Fabrication, Oct. 4–5, 1994, pp. i and 1–8.

Michael J. Ehrlich et al., "Embedded Acoustic Sensors for Process Control and Health Monitoring of Composite Materials", *Nondestructive Characterization of Materials IV*, Plenum Press, New York, 1994, pp. 7–12.

"Material Cure and Internal Stresses Monitored Via Embedded Acoustic Waveguides" by Ronald T. Harrold and Zal N. Sanjana, 1986 International Congress on Technology and Technology Exchange, Pittsburg, PA (Oct. 6–8 1986) pp. 30–33.

*Primary Examiner*—Hezron E. Williams
*Assistant Examiner*—Rose M. Miller
*Attorney, Agent, or Firm*—Gregory Garmong

[57] ABSTRACT

The cure state of a mass of a curable material, such as a composite material formed of a fiber embedded in a curable polymeric matrix, is measured. At least two wire segments are embedded into the mass, and an ultrasonic signal is propagated through the wire segments. From the ultrasonic propagation characteristics, the cure state of the mass is determined.

35 Claims, 6 Drawing Sheets

MEASUREMENT OF THE CURE STATE OF A CURABLE MATERIAL USING AN ULTRASONIC WIRE WAVEGUIDE

BACKGROUND OF THE INVENTION

This invention relates to the measurement of the physical properties of materials, and, more particularly, to the measurement of the cure state of a curable material.

A number of common materials are first prepared in a state which is not hardened and is typically flowable, and are thereafter reacted to harden the material so that it is no longer flowable. In the unhardened, flowable state, the material is readily formed or positioned. Upon hardening, the material is capable of carrying loadings and can serve as a structural material.

Two of the commercially most important such curable materials are certain types of polymers and cement. These materials can be used by themselves, or they can be mixed with other substances to form composite materials: polymer-matrix composite materials in the case of polymers and concrete in the case of cement.

Hardening of such curable materials typically occurs by a chemical crosslinking reaction or a related type of chemical reaction. As used herein, the term "curing" is applied to such reactions, and a "curable" material is one which hardens by such a mechanism. Different terms are sometimes used to describe the hardening reaction. For example, "setting" is sometimes used to describe the hardening of cement, but "curing" will be used herein for all such reactions.

For most practical applications, it is desired that the curable material remain flowable for a period of time and then be controllably curable to the hardened state. Curing is typically accomplished either through the passage of time at ambient temperature, or with an accelerating mechanism such as heating, ultraviolet radiation, or the like. The curing can be accomplished to various intermediate states, and the mechanical and other properties of the curable material depend significantly on the state of cure. An undercured material does not have the required mechanical and other physical properties. Overcuring, on the other hand, can often be as deleterious as undercuring, particularly if overcuring involves the utilization of expensive curing equipment longer than necessary. It is therefore highly important to be able to assess whether and when curing has reached the proper state, so that the curing operation is continued for the proper time.

In some cases, the cure state is readily determined from measurable curing parameters such as the temperature and the elapsed time since initiation of curing, the intensity and duration of exposure to ultraviolet radiation, or other controllable factors. In other cases, the curable material is subject to nonuniformity or other conditions that make estimation of the cure state difficult. For example, in the commonly encountered case where the curable material is fixed to a structural base that acts as a heat sink and the curable material is heated from one side only, the temperature gradient through the curable material makes estimation of the cure state difficult. If instead the curing is accelerated by ultraviolet light, the absorption of the light in the curable material results in less acceleration of the chemical reaction for deeply buried portions than for surface portions, again producing a cure state that is difficult to assess in practice. In another example, large articles made of polymer-matrix composite materials being cured in an autoclave experience different thermal histories at different positions with the article, so that it is difficult to estimate whether proper curing has been achieved at all locations throughout the article. Of course, in all cases the cure state could be measured destructively, but that approach is generally impractical.

There is a need for an approach to the measurement of the cure state of curable materials that is nondestructive, does not interfere with the functioning of the curable material in service, and is straightforward and inexpensive to use. The present invention fulfills this need, and further provides related advantages.

SUMMARY OF THE INVENTION

The present invention provides a method for monitoring the curing of a curable material. Various types of curable materials may be monitored, including curable polymers, cementitious materials, and composite materials based upon these and other types of curable materials. (The composite material is described as curable, because it includes at least one phase that is curable.) The state of cure and optimum curing may be determined from the measured data, or using associated calibration information. The apparatus used in monitoring the state of cure includes an embedded structure in the curable material, which embedded structure is so small that it has little if any adverse effect on the subsequent functionality of the curable material after curing is complete. The present approach is versatile and reliable.

In accordance with the invention, a method of monitoring the curing of a curable material comprises the steps of providing a mass of a curable material that is in an uncured state, the mass having a first surface, and embedding a sensor system in the mass. The sensor system includes at least two wire segments, including a first wire segment having a first end protruding from the first surface and a second end embedded into the mass, and a second wire segment having a second end protruding from the first surface and a first end embedded into the mass. (As used herein, "wire" includes traditional round wires and also non-circular cross-sectional shapes such as flat ribbons.) The mass is cured over a period of time, and the state of cure of the mass is determined simultaneously with the step of curing. The step of determining includes the steps of introducing an ultrasonic signal into the first end of the first wire segment, measuring the propagation of the ultrasonic signal at the second end of the second wire segment, to obtain a propagated signal, and correlating the propagated signal with a state of cure of the mass. The approach may be practiced with either a single continuous wire sensor or a two-wire sensor, or preferably, both used simultaneously.

Preferably, two lengths of wire are used, one bent into an acute-angle shape and the other generally straight, with the two wires in a generally side-by-side relationship to each other and embedded in the curable mass. In accordance with this aspect of the invention, a method of monitoring the curing of a curable material comprises the steps of providing a mass of a curable material that is in an uncured state and embedding at least a portion of each of two lengths of wire in the mass. The step of embedding includes the steps of providing a continuous length of a first wire having a first end, a second end, and an acute-angle bend intermediate the first end and the second end such that the bend is embedded in the mass, and providing a length of a second wire having a first end and a second end, with the first end of the second wire embedded in the mass at a location adjacent to the bend in the length of first wire. The method further includes curing the mass over a period of time, and determining the state of cure of the mass simultaneously with the step of curing. The step of determining includes the steps of introducing an ultrasonic signal into the first end of the first wire, measuring the propagation of the ultrasonic signal at the second end of the first wire to obtain a first propagated signal, measuring the propagation of the ultrasonic signal at the second end of the second wire to obtain a second propagated signal, and correlating the first propagated signal and the second propagated signal with a state of cure of the mass.

One feature of this approach is that two or more sensor systems may be used. Each sensor system is embedded at a different location, in a preferred case to a different distance from the first surface of the mass, so that the state of cure as a function of distance from the first surface may be determined. This capability is particularly important for relatively thin layers of curable reinforcements such as wing skins or where the thin layer is applied to a substrate, and where the curable material is a composite containing graphite reinforcement. In such cases, it is difficult to ensure that uniform curing is achieved throughout the thickness of the thin layer. The present approach provides a direct measure of cure state as a function of position such as depth below the first surface.

The present invention thus provides a technique for directly measuring cure states of curable materials. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
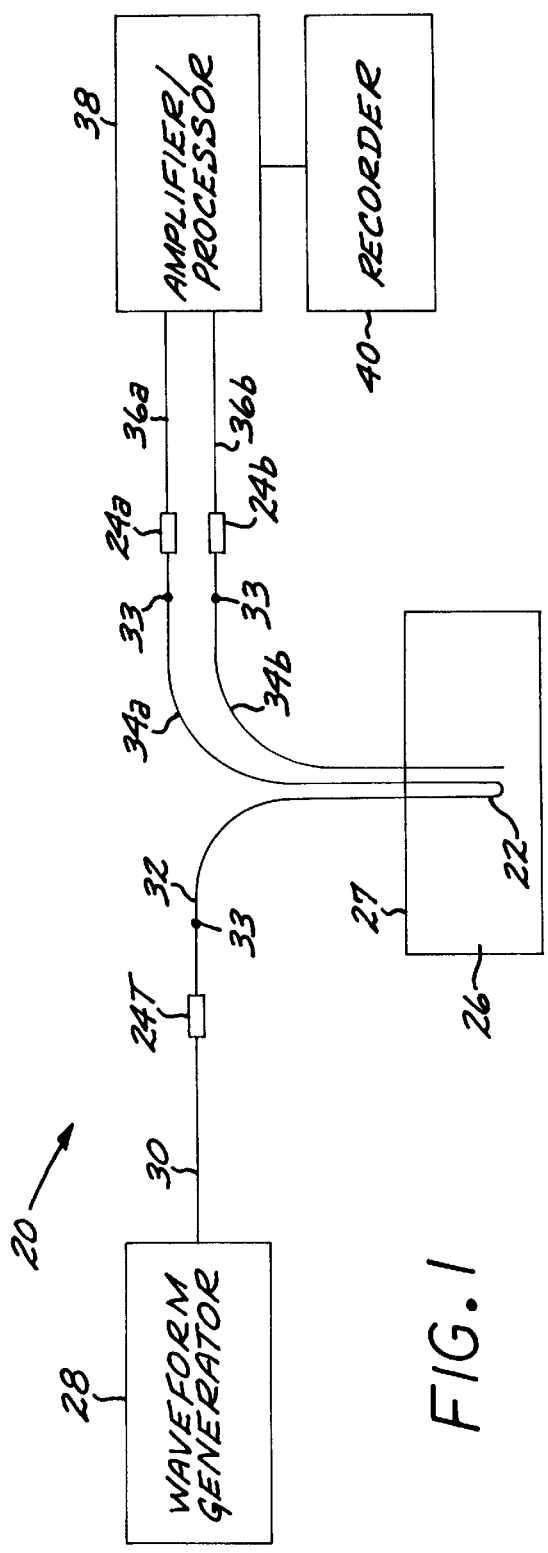
FIG. 1 is a schematic view of a system for monitoring the curing of a curable material.
Figure 4:
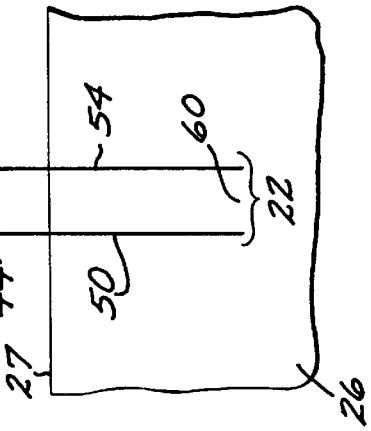
FIG. 4 is a schematic view of a third embodiment of the sensor system.
Figure 3:
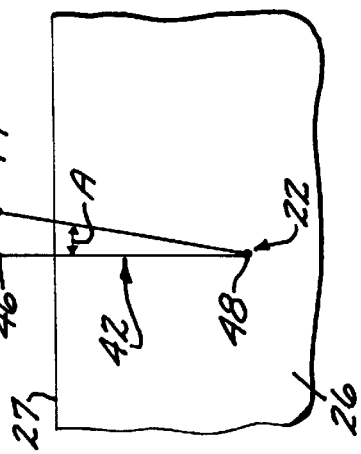
FIG. 3 is a schematic view of a second embodiment of the sensor system.
Figure 2:
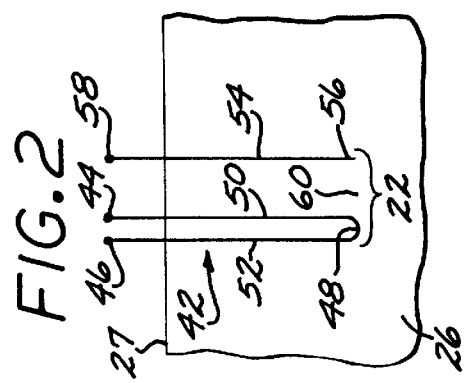
FIG. 2 is a detail of FIG. 1, illustrating the preferred sensor system.
Figure 5A:
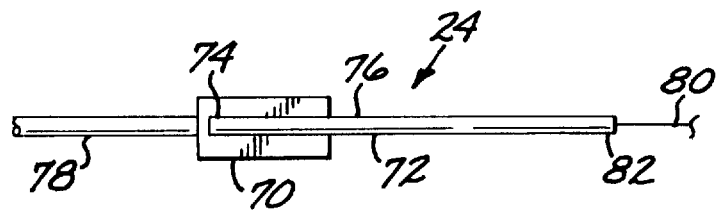
FIG. 5A is a plan view of a piezoelectric transducer used with the invention.
Figure 5B:
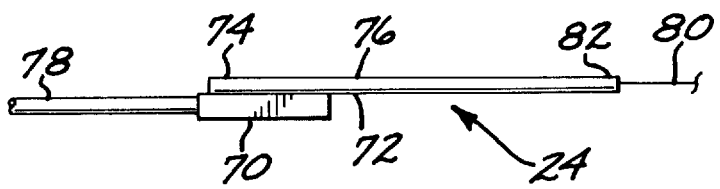
FIG. 5B is an elevational view of the piezoelectric transducer of FIG. 5A.

The present invention preferably utilizes a monitoring system 20 like that shown in FIG. 1, including a sensor system 22 such as those shown in FIGS. 2–4 and transducers 24 such as those shown in FIGS. 5A and 5B. The monitoring system 20 includes the sensor system 22 embedded in a mass 26 of a curable material having a first surface 27. The curable material may be of any type, including but not limited to a curable polymer, a curable (setting) cement, or a composite material incorporating such a curable material as one of its phases. The curable material of most interest to the inventors is a polymer-matrix composite material formed of carbon or graphite fibers embedded in a matrix of a curable polymer such as an epoxy.

The monitoring system 20 includes a waveform generator 28 that produces an electrical signal 30, preferably in the range of from about 20 kilohertz to about 1 megahertz, and most preferably in the range of from about 20 kilohertz to about 200 kilohertz. The waveform is preferably in the form of bursts of signal. The electrical signal 30 excites a transmitter transducer 24T, that provides an ultrasonic signal of the same frequency as the electrical output signal 30 on an ultrasonic transmitted signal wire waveguide 32. The "wire" waveguide may be made of traditional round wires or non-circular cross-sectional shapes such as flat ribbons. A typical operable round wire has a diameter of 0.002 inch or greater, most preferably about 0.005 inch diameter, and a typical flat ribbon has cross-sectional dimensions of 0.005× 0.030 inches. The preferred form of the transducer 24T will be discussed in relation to FIGS. 5A and 5B. The ultrasonic signal on the ultrasonic transmitted signal wire waveguide 32 is provided to the sensor system 22 as its driving signal.

The transducer 24T may be permanently affixed to the wire waveguide 32, or, more preferably, a disconnectable connector 33 may be provided between the two. The connector 33 permits the transducer and waveform generator to be disconnected and used with another sensor system 22. Equivalently for the present purposes, a switch can be provided instead of the connector 33 to permit the transducer 24T and the waveform generator 28 to be switched to another sensor system 22.

One or two received ultrasonic signals on a received ultrasonic signal wire waveguide 34 are received from the sensor system 22, depending upon its configuration to be discussed in relation to FIGS. 2–4. In the preferred case, there are two received ultrasonic signals and two received ultrasonic signal wire waveguides 34a and 34b. The ultrasonic signals on the received ultrasonic signal wire waveguides 34a and 34b are converted to respective electrical signals 36a and 36b by respective transducers 24a and 24b. These electrical signals are amplified and signal processed by an amplifier/processor 38 and recorded by a recorder 40. The waveguides 34a and 34b may be permanently connected to the respective transducers 24a and 24b, or, as discussed above, connected with a disconnectable connector 33 or a switch.

FIGS. 2–4 show three operable configurations of the sensor system 22, with that of FIG. 2 being most preferred. The sensor system 22 of FIG. 2 includes a continuous length of wire 42 having a first end 44, a second end 46, and a generally U-shaped bend 48 therebetween. The first end 44 and the second end 46 protrude from the first surface 27, but much of the length of the wire 42, including the U-shaped bend 48, is embedded within the mass 26 of curable material. The first end 44 communicates with the ultrasonic transmitted wire waveguide 32, and the second end 46 communicates with the received ultrasonic signal wire waveguide 34a. Alternatively, this continuous length of wire 42 may be described as a first length of wire 50, a second length of wire 52, and the bend 48 connecting the first and second lengths.

Figure 10C:
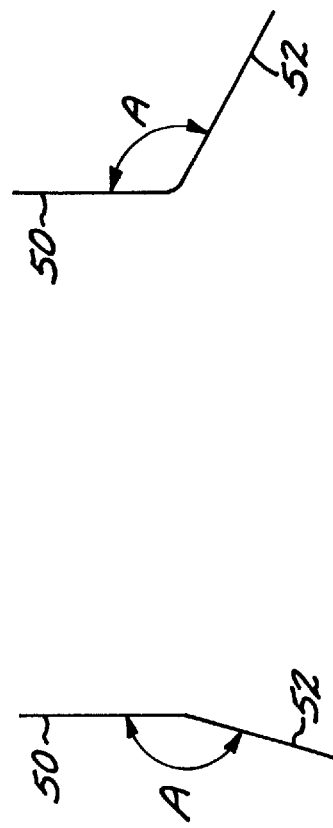
FIGS. 10A, 10B, and 10C are schematic plan views of three configurations of a continuous wire sensor not within the scope of the present claims.
Figure 10B:
Figure 10A:
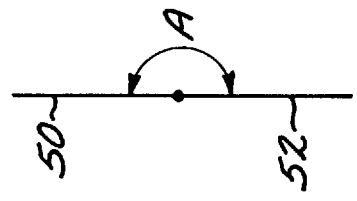

The continuous length of wire 42 may have the lengths 50 and 52 parallel to each other with the bend 48 having a U-shape, as shown, which is convenient for many practical applications. As illustrated in FIGS. 2, 3, 9A–C and 10A–C for some examples, the bend may be characterized by an angle A between the first length of wire 50 and the second length of wire 52. The angle A is measured through the shortest arc between the two wires 50 and 52 and is therefore always 180 degrees or less. To be operable in the present invention, the angle A of the bend 48 lies in the range of 90 degrees or less, termed herein an "acute" bend, shown for several examples in FIGS. 2, 3, and 9A–9C. (In the embodiment of FIG. 2, the angle A is 0 degrees with the wires 50 and 52 parallel to each other, a configuration that is within the definition of "acute" bend.) In all such configurations, each of the lengths 50 or 52 has a component of its length laterally displaced from that of the other length. It is critical that at least some geometric component of the lengths 50 and 52 exist in a laterally displaced arrangement such as results from an acute bend. This geometry is to be contrasted with one where the angle A of the bend 48 is greater than 90 degrees and as large as 180 degrees, termed herein an "obtuse bend", three examples of which are illustrated in FIGS. 10A–10C. One special case is an angle A of 180 degrees, a straight wire such as shown in FIG. 10A. An obtuse bend, including a straight wire 42, is not operable with the present invention because there are no laterally displaced components of the lengths of the segments 50 and 52.

A separate length of wire 54 has a first end 56 positioned at about the same distance from the first surface 27 as the U-shaped bend 48 and a second end 58 protruding out of the first surface 27. The first end 56 is separated and spaced apart from the bend 48 by a gap 60, so that some of the curable material of the mass 26 lies between the bend 48 and the first end 56. The second end 58 communicates with the received ultrasonic signal wire waveguide 34b.

The second embodiment of FIG. 3 includes only a continuous length of wire 42, and the third embodiment of FIG. 4 includes only a wire segment 42 and a wire segment 54. In the embodiment of FIG. 3, the acute bend 48 is generally of a "V-shape", and such an alternative configuration for the bend 48 is encompassed within the term "acute bend". The bend 48 in this case is slightly greater than 0 degrees. In the embodiment of FIG. 4, the segment 50 communicating with the ultrasonic output signal 32 is present, but there is no bend and no second segment 52 as found in the embodiment of FIG. 2. The structure and interconnections of these embodiments are otherwise the same as described in FIG. 2, and that description and the reference numerals are incorporated here.

The preferred form used in all of the transducers 24T, 24a, and 24b is illustrated in FIGS. 5A and 5B. A piezoelectric element 70 is affixed to an outside surface 72 at a first end 74 of a length of tubing 76, typically by soldering. A preferred piezoelectric element is PZT 5A lead-zirconate-titanate, available commercially from Keromos or Vernitron, but other piezoelectric materials such as magnesium niobate or sodium potassium niobate may be used. A preferred tubing 76 is 20 gauge stainless steel tubing have an outside diameter of about 0.035 inches and an inside diameter of about 0.023 inches, with a length of about ½ inch. An electrical coaxial cable 78 communicates with the piezoelectric element 70. A wire waveguide 80 is affixed into a oppositely disposed second end 82 of the length of tubing 72.

When the transducer 24 is to be used as the transmitting transducer 24T, the coaxial cable 78 carries the electrical output signal 30 and the wire waveguide 80 is the ultrasonic transmitted waveguide 32. When the transducer 24 is to be used as the receiving transducer 24a or 24b, the coaxial cable 78 carries the received electrical signal 36 and the wire waveguide 80 is the received ultrasonic signal wire waveguide 34a or 34b, respectively.

The mass of curable material 26 may be a stand-alone element, as shown in FIG. 1. In other cases, the mass of curable material 26 may be affixed to a structural base. Whether the mass of curable material 26 is a stand-alone element or affixed to a structural base, there may be a single sensor system 22, as in FIG. 1, or multiple sensor systems used to determine the curing state at different locations within the mass.

Figure 6:
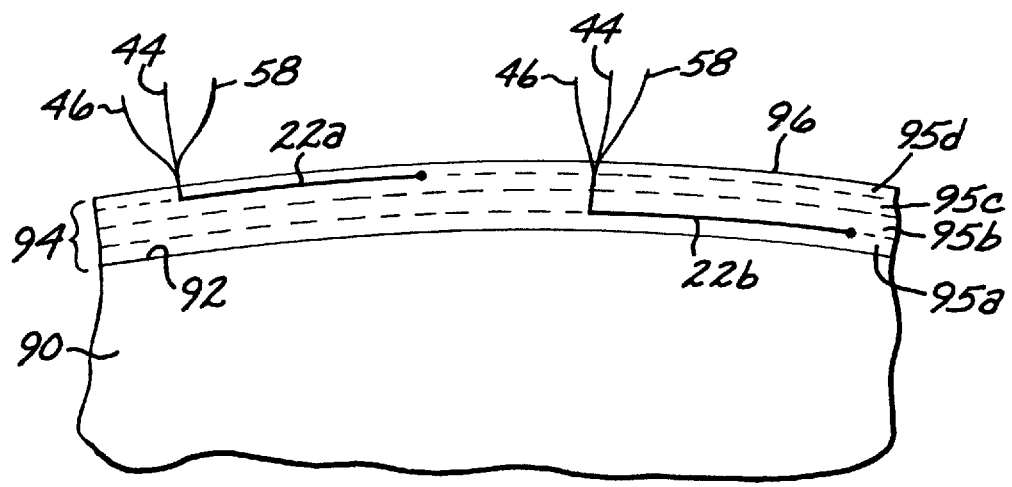
FIG. 6 is a schematic sectional view of a mass of curable composite material wrapped onto a column and being cured in place, with a first sensor system located at a first distance below the surface and a second sensor system located at a second distance below the surface.

FIG. 6 illustrates in cross sectional view a column 90 such as a bridge support column which has been wrapped on its outer surface 92 with a jacket or casing 94 formed of multiple layers 95a, 95b, 95c, and 95d of a curable composite material. A first sensor system 22a is embedded at a first depth below a surface 96 of the casing 94, between the layers 95a and 95b, and a second sensor system 22b is embedded at a second depth below the surface 96, between the layers 95c and 95d. (In practice, there would be more layers, and a sensor system may be embedded between each pair of layers, as desired. Only two sensor systems 22a and 22b are shown in FIG. 6 for clarity of illustration.) The individual embedded portions of the wires of the sensor systems 22a and 22b lie parallel to the surfaces 92 and 96, so that curing state information may be determined at the preselected distances below the surface 96. Accordingly, the individual wires are not visible in FIG. 6, but the wire ends 44, 46, and 58 may be seen as protruding from the surface 96. The preferred sensor system of FIG. 2 is depicted in FIG. 6, but other sensor systems such as those of FIGS. 3 and 4 could instead be used. For each of the sensor systems 22a and 22b, there are provided the other elements of the monitoring system 20 described in relation to FIG. 1. Separate monitoring systems may be used, or the inputs and outputs of a single monitoring system may be manually connected, multiplexed, or switched with the various sensor systems, inasmuch as the curing times would normally permit the required measurements to be made with a multiplexed or switched system. Although illustrated in relation to the preferred embodiment of a wrapped column, the approach may be used in relation to other articles such as large, complex structural elements being cured by heat in an autoclave.

The approach of FIG. 6 permits the state of cure to be determined as a function of location within the mass, in this case the location being indicated by the distance below the surface 96. This capability is important in a wide variety of practical applications. In one such application of interest to the inventors, the column 90 is a bridge support column several feet in diameter. The layers 95 are wrapped onto the column to form the casing 94 in the uncured state and thereafter cured by heating or exposure to ultraviolet light. The heating or ultraviolet light source is located external to the surface 96, so that the layer 95d receives the greatest energy input and the layer 95a receives the least energy input. Moreover, the column 90 acts as a heat sink, further reducing the temperature of the layer 95a and causing it to cure more slowly than the outermost layer 95d. If only the cure state of the layer 95d were monitored and curing decisions based upon that information, it is possible that the layer 95a would be undercured. Although the circumstances discussed above ensure that all of the layers 95 will never be cured to exactly the same state, monitoring the cure states of all of the layers 95 allows optimization of the curing processing.

Figure 11:
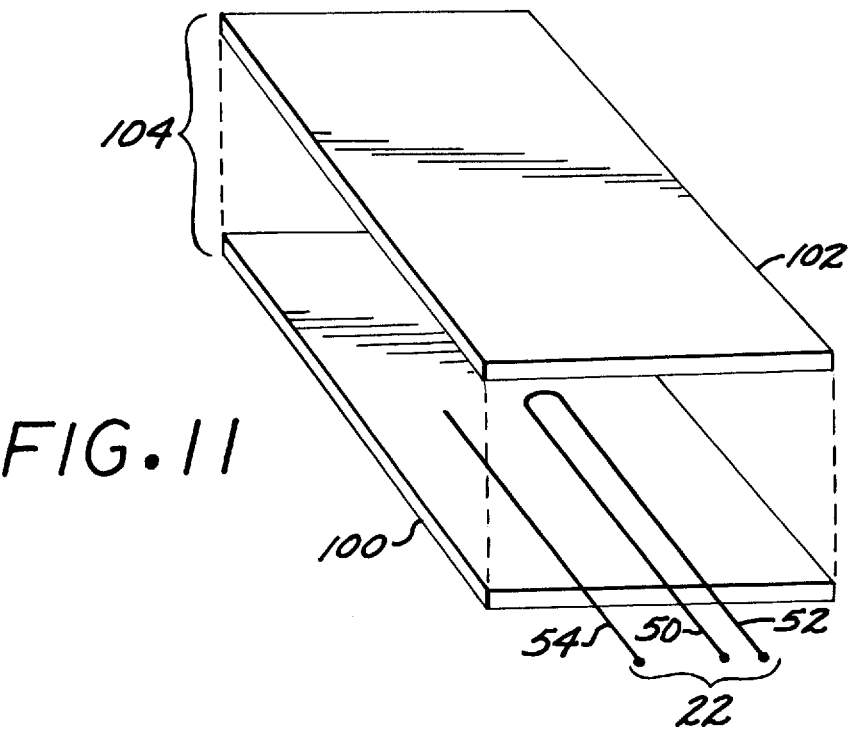
FIG. 11 is an exploded perspective view of a patch configuration for the sensor system.
Figure 9C:
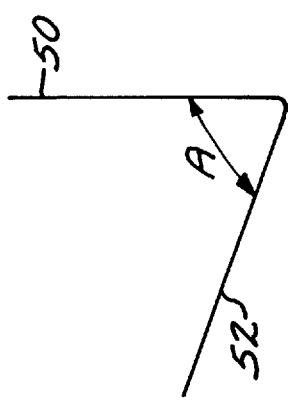
FIGS. 9A, 9B, and 9C are schematic plan views of three operable configurations for the continuous wire sensor.
Figure 9B:
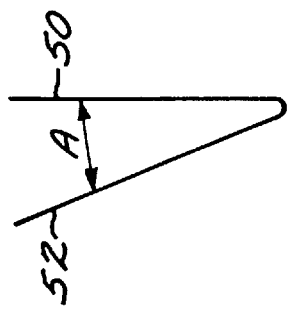
Figure 9A:
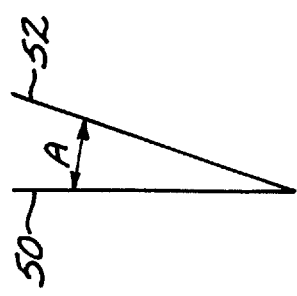

FIG. 11 illustrates one form of a patch structure with which the sensor system 22 may be readily handled and applied in situations such as that shown in FIG. 6. The wires 50, 52, and 54 of the sensor system 22 are positioned on a substrate 100. The wires are typically held in place on the substrate with a drop of curable adhesive. A top 102 is applied over the substrate 100 and fixed in place, typically with a small amount of adhesive or by slightly heating the substrate and the top to fuse them together. The substrate 100 and the top 102 are each preferably selected to be one or two plies of the same material as the material whose curing behavior is to be determined, in the case of FIG. 6 the material of the layers 95. The substrate 100, top 102, and sensor system 22 together form a patch 104 that may be readily handled and placed between the layers 95.

Figure 7:
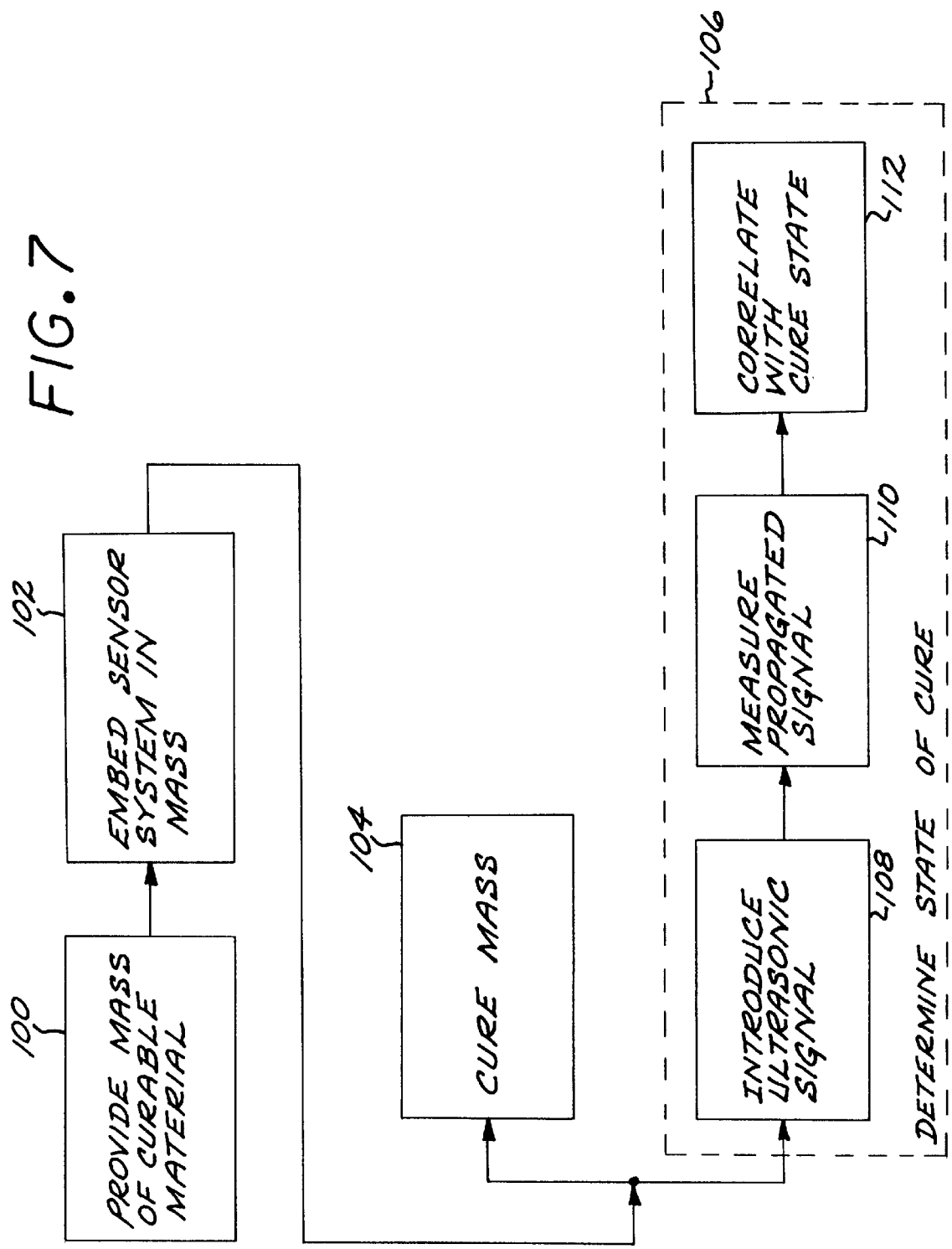
FIG. 7 is a block diagram of an approach for practicing the invention.

FIG. 7 is a block flow diagram of an approach for practicing the invention. The mass of curable material, either in a stand-alone form or affixed to a structural base, is provided, numeral 100. The sensor system 22 is embedded in the mass, numeral 102. The steps 100 and 102 are typically accomplished in an interrelated manner, with the sensor system(s) being embedded in the mass as the mass is being prepared. For example, in the multilayer mass such as shown in FIG. 6, the first layer 95a is wound onto the column 90, and the sensor system 22b is placed onto the exposed surface of the first layer 95a. The second layer 95b and the third layer 95c are wound overlying the first layer 95a, so that the sensor system 22b is captured and embedded between the first layer 95a and the second layer 95b. The sensor system 22a is placed onto the exposed surface of the third layer 95c and the fourth layer 95d is would overlying the third layer 95c, so that the sensor system 22a is captured and embedded between the third layer 95c and the fourth layer 95d. After this winding operation is complete, the mass of curable material is cured, numeral 104, and its cure state is simultaneously monitored, numeral 106. Curing is typically accomplished by placing a heater or ultraviolet source adjacent to the external surface 96 of the mass. To determine of the state of cure, numeral 106, an ultrasonic signal is introduced into the sensor system, numeral 108, at the first end 44. The propagated signal at the ends 46 and/or 58 is measured, numeral 110, depending upon the type of sensor system used. The propagated signal is correlated with the cure state, numeral 112.

Figure 8:
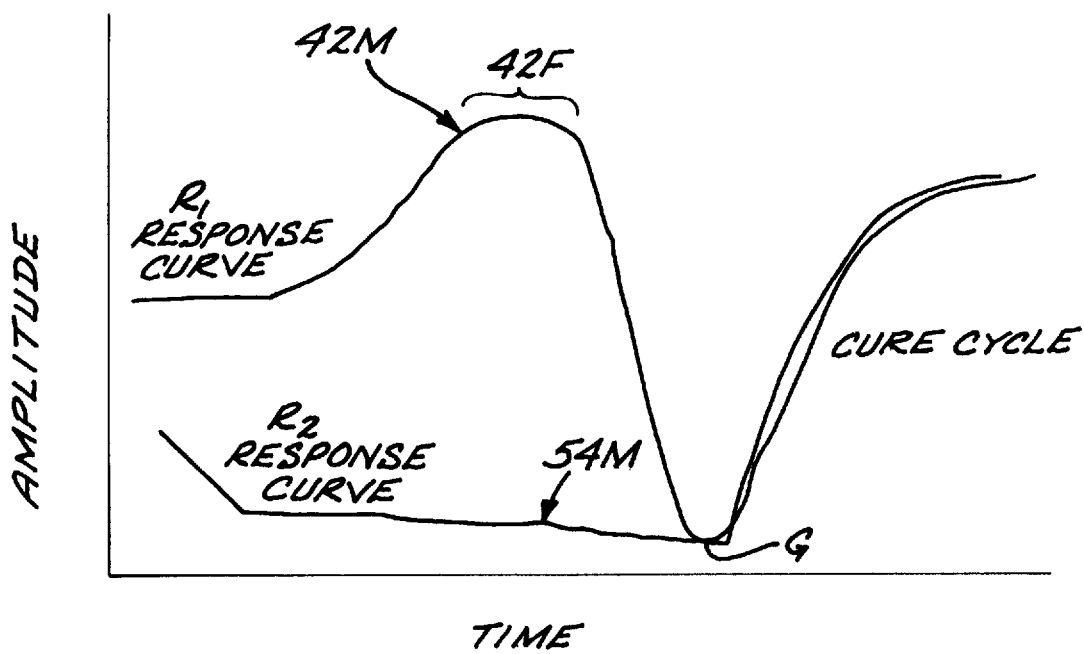
FIG. 8 is a measured curing response curve obtained with the approach of the invention.

A monitoring system 20 as described was constructed, using the general arrangement of FIG. 1, the sensor system of FIG. 2, and the transducers of FIGS. 5A and 5B. The curing of a composite material formed of graphite fibers in a curable epoxy matrix was monitored. FIG. 8 depicts actual measured results for this system. For the continuous wire sensor 42, a response curve 42M is measured. For signals transmitted from the wire segment 50, through the curing epoxy material in the gap 60, and to the wire segment 54, a response curve 54M is measured. The curves 42M and 54M are initially widely separated prior to the gel point G of the curable polymeric matrix material. The curve 42M passes through a maximum range 42F, associated with the flow of the curable polymer prior to curing. Prior to the gelling of the polymer, nearly all of the ultrasonic energy introduced into the wire segment 50 at the first end 44 is transmitted along the length of the wire sensor 42 and received at the second end 46. There is little energy transferred out of the wire 50, through the gap 60, and into the wire 54. As the polymer begins to polymerize or gel at point G, the wire segment 50 is constricted by the polymerizing polymer so that energy is transferred out of the wire segment 50 and into the wire segments 52 and 54. The output signals 42M and 54M thereafter become substantially the same, because in each case the energy transmitted to the respective output ends 46 and 58 is conducted from the wire 50 and through the polymer material.

This last-discussed observation demonstrates the advantage of the present approach over using a straight wire or a wire with some other obtuse-angle bend. In those cases, after the gel point G is passed the attenuation of energy within the wire 50 becomes so great that the signal amplitude transmitted the length of the wire becomes ever smaller and more difficult to measure. In the present approach using an acute-angle bend in the wire as in FIG. 3 and/or two laterally separated wires as in FIG. 4, the energy transferred laterally outwardly from the wire 50 is received by the wire 52 and/or the wire 54 to provide a measurable quantity. The present approach may therefore be practiced using either of the sensor systems of FIGS. 3 or 4, but the combined approach of FIG. 2 is preferred to yield the maximum information about the curing behavior of the curable material.

The ultrasonic property preferably measured in the sensor system 22 is the signal amplitudes received by the transducers 24a and 24b relative to the signal amplitude transmitted by the transducer 24T. The time of flight of the ultrasonic signal may also be measured and used, but it is less sensitive to curing behavior than amplitude measures and is therefore not preferred.

Figure 12:
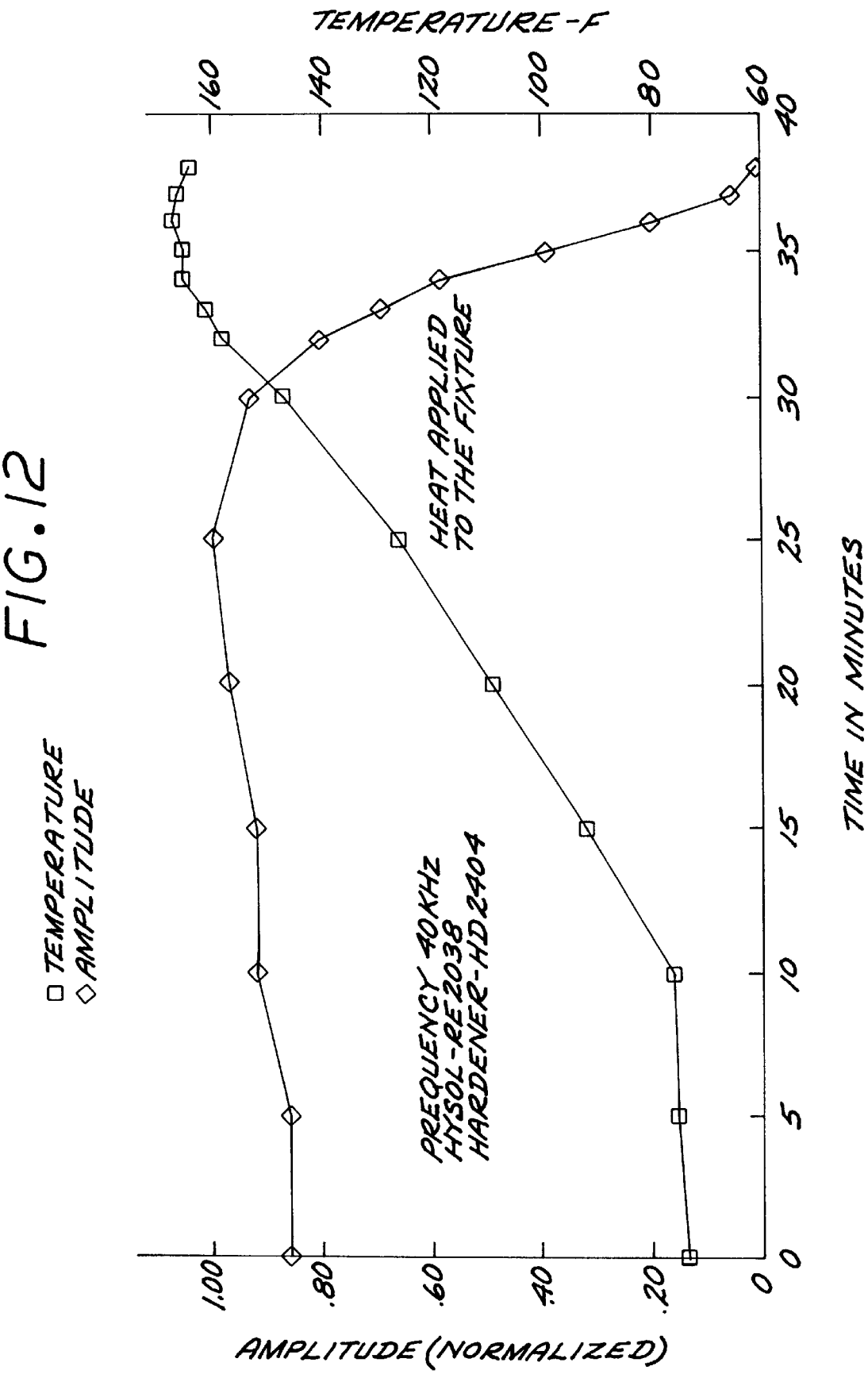
FIG. 12 is a measured curing response curve for a straight wire sensor.

Comparative testing of an embodiment not within the scope of the invention has been performed using an apparatus like that of FIG. 1, except with the straight-wire configuration illustrated in FIG. 10A. FIG. 12 depicts the results obtained, which may be compared with those of FIG. 8. in the approach of the invention, producing the results of FIG. 8, the measured amplitude shows the well-defined gel point G and the indication of polymer flow in the region 42F. After the gel point G has been passed with increasing time, the amplitude increases so that it can be readily monitored. In the approach using a straight wire, producing the results of FIG. 12, there is no well-defined indication of flow, gelling, or curing of the polymer. The amplitude decreases with increasing time in the region where gelling and curing occurs as energy is bled from the wire into the polymer material, making further measurements difficult.

The data such as that depicted in FIG. 8 is useful in itself, as the fully cured state may be judged from the time past the gel point G at which the curves become horizontal or nearly so. The data may be made quantitative by performing calibrations in which the data of FIG. 8 is gathered in laboratory conditions for a number of specimens whose cure state is independently determined, as by destructive measurements. The independently determined cure state is correlated with the data of FIG. 8, so that the actual cure state under field conditions may be determined from the ultrasonic measurements using the wire wave guides.

Tests have also been performed using an experimental arrangement simulating that depicted in FIG. 6, with sensors embedded at different depths from the heated surface of the curable mass. These tests demonstrate that the curing behavior prior to reaching the gel point, the gel point itself, and the curing behavior after passing the gel point may be determined as a function of location within the curing mass.

Although these tests have been performed using the polymeric-matrix composite materials of greatest interest to the inventors, the same principles and procedures are applicable to measurements of other curable materials such as cement and concrete.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method of monitoring the curing of a curable material, comprising the steps of:
    providing a mass of a curable material that is initially in an uncured state;
    embedding a sensor system in the mass, the sensor system including at least two wires, including
        a fist wire having
            a first end,
            a second end, and
            an acute angle bend intermediate the first end and the second end and embedded in the mass, and
        a second which is not continuous with the first wire, the second wire having
            a first end embedded into the mass at a location adjacent to the acute angle bend of the first wire and spaced apart therefrom, so that some of the curable material lies between the acute angle bend and the second wire, and
            a second end;
    curing the mass over a period of time;
    determining the state of cure of the mass simultaneously with the step of curing, the step of determining including the steps of
        introducing an ultrasonic signal into the first end of the first wire,
        measuring the propagation of the ultrasonic signal at the second end of the first wire, to obtain a first propagated signal,
        measuring the propagation of the ultrasonic signal at the second end of the second wire segment, to obtain a second propagated signal, and
        correlating the first propagated signal and the second propagated signal with a state of cure of the mass.

2. The method of claim 1, wherein the step of providing includes the step of
    providing a composite material having fibers embedded in a curable polymeric matrix.

3. The method of claim 1, wherein the step of providing includes the step of
    providing a curable cementitious material.

4. The method of claim 1, where the step of introducing includes the step of
    introducing a tone-burst ultrasonic signal into the first end of the first wire.

5. The method of claim 1, wherein the step of introducing includes the step of
    affixing a piezoelectric transducer to the second end of the first wire.

6. The method of claim 1, wherein the step of measuring the first propagated signal includes the step of
    affixing a piezoelectric transducer to the second end of the first wire.

7. The method of claim 1, wherein the step of introducing includes the step of
    introducing an ultrasonic signal having a frequency of from about 20 kilohertz to about 1 megahertz.

8. The method of claim 1, wherein the step of measuring the first propagated signal, includes the step of
    measuring the amplitude of the ultrasonic signal.

9. The method of claim 1, including the additional steps of
    forming a calibration relation between ultrasonic propagation in the curable material and the state of cure of the curable material, and
    utilizing the calibration relation in the step of correlating.

10. A method of monitoring the curing of a curable material, comprising the steps of:
    providing a mass of a curable material that is in an uncured state, the mass having a first surface;
    embedding a sensor system in the mass, the sensor system including at least two wire segments including
        a first wire segment having
            a first end, and
            a second end embedded into the mass, and
        a second wire segment having
            a first end embedded into the mass, and
            a second end,
    wherein the step of embedding includes the step of providing the first wire segment and the second wire segment with the second end of the first wire segment connected to the first end of the second wire segment by an acute-angle bend;
    curing the mass over a period of time;
    determining the state of cure of the mass simultaneously with the step of curing, the step of determining including the steps of
        introducing an ultrasonic signal into the first end of the first wire segment,
        measuring the propagation of the ultrasonic signal at the second end of the second wire segment, to obtain a propagated signal, and
        correlating the propagated signal with a state of cure of the mass.

11. The method of claim 10, wherein the step of embedding includes the step of
    providing a continuous length of wire having a first end and a second end and the bend therein, the first segment being the portion between the first end and the bend, and the second segment being the portion between the bend and the second end, and wherein
    the step of introducing includes the step of
        introducing the ultrasonic signal into the first end of the continuous length of wire, and wherein
    the step of measuring includes the step of
        measuring the propagated signal at the second end of the continuous length of wire.

12. The method of claim 10, wherein the step of embedding includes a step of
    embedding a third wire segment into the mass, the third wire segment having a first end adjacent to the acute angle bend but spaced apart therefrom, so that some of the curable material of the mass lies between the acute angle bend and the first end of the third wire segment.

13. The method of claim 10, wherein the step of providing includes the step of
    providing a composite material having fibers embedded in a curable polymeric matrix.

14. The method of claim 10, wherein the step of providing includes the step of
    providing a curable cementitious material.

15. The method of claim 10, wherein the step of introducing includes the step of
    introducing a tone-burst ultrasonic signal into the wire.

16. The method of claim 10, wherein the step of introducing includes the step of
    affixing a piezoelectric transducer to the wire.

17. The method of claim 10, wherein the step of measuring includes the step of affixing a piezoelectric transducer to the wire.

18. The method of claim 10, wherein the step of introducing includes the step of
introducing an ultrasonic signal having a frequency of from about 20 kilohertz to about 1 megahertz.

19. The method of claim 10, wherein the step of measuring includes the step of
measuring the amplitude of the ultrasonic signal.

20. The method of claim 10, including the additional steps of
forming a calibration relation between ultrasonic propagation in the curable material and the state of cure of the curable material, and
utilizing the calibration relation in the step of correlating.

21. A method of monitoring the curing of a curable material, comprising the steps of:
providing a mass of a curable material that is in an uncured state, the mass having a first surface, wherein the step of providing a mass includes the step of affixing the mass of the curable material to a structural base;
embedding a sensor system in the mass, the sensor system including at least two wire segments including
a first wire segment having
a first end,
and a second end embedded into the mass, and
a second wire segment having
a first end embedded into the mass, and
a second end;
curing the mass over a period of time;
determining the state of cure of the mass simultaneously with the step of curing, the step of determining including the steps of
introducing an ultrasonic signal into the first end of the first wire segment,
measuring the propagation of the ultrasonic signal at the second end of the second wire segment, to obtain a propagated signal, and
correlating the propagated signal with a state of cure of the mass.

22. The method of claim 21, wherein the structural base is a column, and wherein the step of embedding includes the step of
winding the two wire segments circumferentially around the column.

23. The method of claim 21, wherein the step of providing includes the step of
providing a composite material having fibers embedded in a curable polymeric matrix.

24. The method of claim 21, wherein the step of providing includes the step of
providing a curable cementitious material.

25. The method of claim 21, wherein the step of introducing includes the step of
introducing a tone-burst ultrasonic signal into the wire.

26. The method of claim 21, wherein the step of introducing includes the step of
affixing a piezoelectric transducer to the wire.

27. The method of claim 21, wherein the step of measuring includes the step of
affixing a piezoelectric transducer to the wire.

28. The method of claim 21, wherein the step of introducing includes the step of
introducing an ultrasonic signal having a frequency of from about 20 kilohertz to about 1 megahertz.

29. The method of claim 21, wherein the step of measuring includes the step of
measuring the amplitude of the ultrasonic signal.

30. The method of claim 21, including the additional steps of
forming a calibration relation between ultrasonic propagation in the curable material and the state of cure of the curable material, and
utilizing the calibration relation in the step of correlating.

31. A method of monitoring the curing of a curable material, comprising the steps of:
providing a mass of a curable material that is in an uncured state;
embedding at least a portion of each of two lengths of wire in the mass, the step of embedding including the steps of;
providing a continuous length of a first wire having a first end, a second end, and an acute-angle bend intermediate the first end and the second end such that the bend is embedded in the mass, and
providing a length of a second wire having a first end and a second end, the first end of the second wire being embedded in the mass at a location adjacent to and laterally displaced from the bend in the length of first wire;
curing the mass over a period of time;
determining the state of cure of the mass simultaneously with the step of curing, the step of determining including the steps of
introducing an ultrasonic signal into the first end of the first wire,
measuring the propagation of the ultrasonic signal at the second end of the first wire to obtain a first propagated signal,
measuring the propagation of the ultrasonic signal at the second end of the second wire to obtain a second propagated signal, and
correlating the first propagated signal and the second propagated signal with a state of cure of the mass.

32. A method of monitoring the curing of a curable material, comprising the steps of:
providing a mass of a curable material that is in an uncured state, the mass having a first surface;
embedding a first sensor system in the mass at a first distance below the first surface, the first sensor system including at least two wire segments including
a first wire segment having a first end protruding from the first surface and a second end embedded into the mass, and
a second wire segment having a second end protruding from the first surface and a first end embedded into the mass;
embedding a second sensor system in the mass at a second distance below the first surface, the second sensor system including at least two wire segments including
a first wire segment having
a first end, and
a second end embedded into the mass, and
a second wire segment having
a first end embedded into the mass, and
a second end;
curing the mass over a period of time;
determining the state of cure of the mass simultaneously with the step of curing, the step of determining including the steps of introducing a first ultrasonic signal into the first end of the first wire segment of the first sensor, measuring the propagation of the ultrasonic signal at the second end of the second wire segment of the first sensor, to obtain a first propagated signal, and introducing a second ultrasonic signal into the first end of the first wire segment of the second sensor, measuring the propagation of the ultrasonic signal at the second end of the second wire segment of the first sensor, to obtain a second propagated signal, and correlating the first and-second propagated signals with a state of cure of the mass as a function of distance from the first surface.

33. The method of claim 32, wherein the step of providing a mass includes the step of affixing the mass of the composite material to a column as an overlayer.

34. The method of claim 33, wherein the step of embedding includes the step of winding the wires of the first sensor system and the second sensor systems circumferentially around the column.

35. The method of claim 32, wherein the wires of the first sensor system and the second sensor system lie substantially parallel to the first surface.

\* \* \* \* \*